United States Patent
Melsheimer (10) Patent No.: US 8,075,607 B2
(45) Date of Patent: Dec. 13, 2011

(54) CONTROL HANDLE

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 724 days.

(21) Appl. No.: 11/965,164

(22) Filed: Dec. 27, 2007

(65) Prior Publication Data

US 2009/0171433 A1 Jul. 2, 2009

(51) Int. Cl.
*A61F 2/06* (2006.01)
*A61F 2/24* (2006.01)

(52) U.S. Cl. ...................................... 623/1.11; 623/2.11

(58) Field of Classification Search ................. 623/1.11, 623/2.11; 606/1, 108; 604/508; 600/131
See application file for complete search history.

(56) References Cited

U.S. PATENT DOCUMENTS

| | | | |
|---|---|---|---|
| 3,051,172 A | 8/1962 | Bruchhaus | |
| 5,409,478 A | 4/1995 | Gerry et al. | |
| 5,454,827 A * | 10/1995 | Aust et al. | 606/170 |
| 5,618,300 A | 4/1997 | Marin et al. | |
| 5,741,270 A | 4/1998 | Hansen et al. | |
| 5,833,694 A | 11/1998 | Poncet | |
| 5,944,727 A | 8/1999 | Ahari et al. | |
| 5,968,052 A | 10/1999 | Sullivan, III et al. | |
| 6,238,402 B1 | 5/2001 | Sullivan, III et al. | |
| 6,391,050 B1 | 5/2002 | Broome | |
| 6,514,261 B1 | 2/2003 | Randall et al. | |
| 6,599,296 B1 | 7/2003 | Gillick et al. | |
| 6,755,854 B2 | 6/2004 | Gillick et al. | |
| 6,755,855 B2 * | 6/2004 | Yurek et al. | 623/1.12 |
| 6,796,935 B1 * | 9/2004 | Savino | 600/7 |
| 7,105,016 B2 | 9/2006 | Shiu et al. | |
| 2003/0028236 A1 * | 2/2003 | Gillick et al. | 623/1.11 |
| 2003/0040789 A1 | 2/2003 | Colgan et al. | |
| 2003/0144671 A1 | 7/2003 | Brooks et al. | |
| 2005/0021123 A1 | 1/2005 | Dorn et al. | |
| 2005/0090890 A1 * | 4/2005 | Wu et al. | 623/1.11 |
| 2007/0244540 A1 * | 10/2007 | Pryor | 623/1.11 |
| 2008/0319524 A1 * | 12/2008 | Yachia et al. | 623/1.11 |

* cited by examiner

*Primary Examiner* — Julian Woo
*Assistant Examiner* — Christopher L Templeton
(74) *Attorney, Agent, or Firm* — Brinks Hofer Gilson & Lione (57) ABSTRACT

A delivery device for deploying an expandable prosthesis and method of use are described. The delivery device comprises a handle that comprises a trigger. Activation of the trigger enables incremental retraction of an outer sheath to expose a self-expanding prosthesis. Activation and subsequent deactivation of the trigger causes a movable member to ratchedly engage with a stationary rack and a trigger rack.

19 Claims, 6 Drawing Sheets

CONTROL HANDLE

TECHNICAL FIELD

This invention relates to a medical device and, in particular to a delivery device for a self-expanding prosthesis and a method of delivering and deploying the prosthesis into a body lumen.

BACKGROUND

A self-expanding prosthesis is typically introduced into the body using a delivery device that comprises a push-pull mechanism. The delivery device comprises an outer catheter coaxially disposed and slidable over an inner catheter. The prosthesis is disposed at the distal end of the device between the inner catheter and the outer catheter. The inner and outer catheters are preferably coaxial and move longitudinally with respect to each other. The prosthesis may be deployed by proximally pulling back on the outer catheter relative to the inner catheter until the prosthesis is exposed.

There are numerous drawbacks to the above push-pull delivery device. For example, utilizing a conventional push-pull delivery device may cause the physician to inadvertently use excessive force and pull back on the outer catheter too far, thereby prematurely deploying the prosthesis in an incorrect position within a body lumen. At this step in the procedure, repositioning of the prosthesis becomes difficult, if not impossible, because the prosthesis has already radially self-expanded into the body lumen. Additionally, controlled retraction of the outer sheath may not be possible because the physician may only have coarse control over manually retracting the outer catheter. Such coarse, manual retraction of the outer catheter may lead to inadvertent jerking of the outer catheter. Furthermore, two hands are typically needed to deploy the prosthesis with a push-pull mechanism. One hand may be required to hold the inner catheter while the other hand pulls the outer catheter and slides it back over the inner catheter. The use of two hands prevents the physician from performing another task during the procedure.

Accordingly, in view of the drawbacks of current technology, there is a desire for a delivery system that can increase the control, accuracy and ease of placement during deployment of a prosthesis. Although the inventions described below may be useful for increasing the control, accuracy and ease of placement during deployment of the prosthesis, the claimed inventions may also solve other problems.

SUMMARY

Accordingly, a delivery device is provided comprising a control handle that is capable of incrementally retracting an outer sheath in a controlled manner.

The invention may include any of the following aspects in various combinations and may also include any other aspect described below in the written description or in the attached drawings.

In a first aspect, a delivery device is provided. The delivery device comprises a handle which further comprises a trigger attached to a housing. The handle comprises a passageway therein. A trigger rack is affixed to the trigger, the trigger rack being movable back and forth within the passageway of the handle. A stationary rack is affixed to the housing. A movable member is disposed within the passageway. The movable member is ratchedly engaged to the trigger rack and the stationary rack. A distal end of the movable member is adapted to be affixed to a proximal end of an elongate sheath. The ratcheted engagement of the movable member with the trigger and the stationary racks is configured to proximally retract the elongate sheath.

In a second aspect, a delivery system is provided. The handle comprises a trigger attached to a housing. The handle comprises a passageway therein. An inner sheath is provided that extends into the handle. An outer sheath is provided that coaxially disposes over the inner sheath and extends into the handle. A prosthesis is disposed between the inner sheath and the outer sheath. A trigger rack is affixed to the trigger. The trigger rack is movable back and forth within the passageway of the handle. A stationary rack is affixed to the housing. A movable member is disposed within the passageway. The movable member is ratchedly engaged to the trigger rack and the stationary rack. A distal end of the movable member is affixed to a proximal end of the outer sheath. The ratcheted engagement of the movable member with the trigger and the stationary racks proximally retracts the outer sheath to deploy the prosthesis.

BRIEF DESCRIPTION OF THE DRAWINGS

Embodiments will now be described by way of example with reference to the accompanying drawings, in which:

FIGS. 4*a*-7*b* show a method of use of the delivery device;

DETAILED DESCRIPTION OF THE PREFERRED EMBODIMENTS

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

Throughout the specification, the terms "distal" and "distally" shall denote a position, direction, or orientation that is generally away from the handle. Accordingly, the terms "proximal" and "proximally" shall denote a position, direction, or orientation that is generally towards the handle.

Referring now to the drawings in FIGS. 1-9, a delivery device for deploying a self-expanding prosthesis is shown. As will be discussed, the delivery device has the ability to incrementally retract an outer sheath in a controlled manner while maintaining the inner sheath fixated, thereby gradually uncovering the prosthesis. One-handed operation of the delivery device is also possible.

Figure 1:
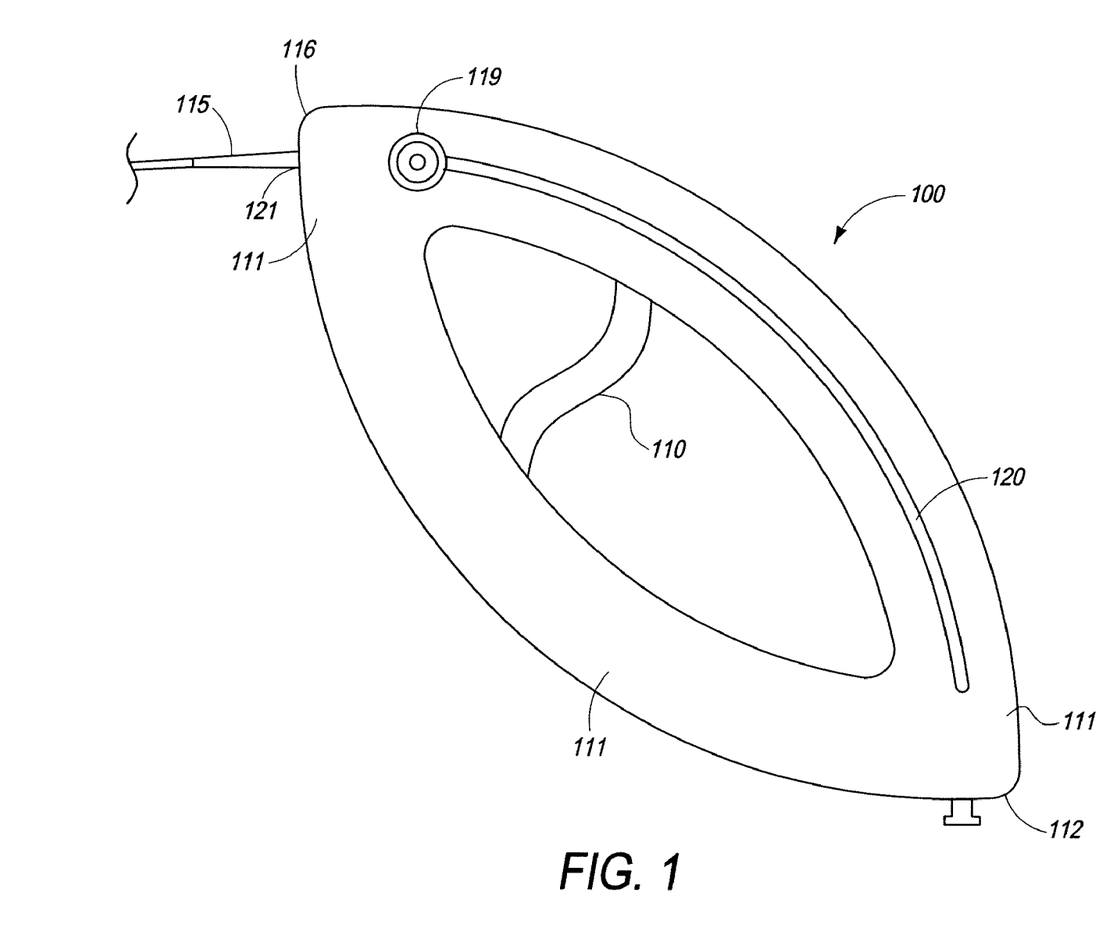
FIG. 1 shows a delivery device in which the handle is symmetrically shaped.

FIG. 1 shows an exemplary delivery device. The delivery device comprises a handle 100. The handle 100 includes a trigger 110 assembled to a housing 111. A user may activate the handle 100 by pulling on the trigger 110 such that the trigger 110 is pulled towards the proximal end 112 of the handle 100. Such actuation of the trigger 110 enables incremental retraction of the outer sheath to expose a self-expanding prosthesis. Conversely, the sideport hub may be grasped disitally and pulled proximally to cause the sheath 115 to be retracted under relatively faster, coarser control, as will be explained in greater detail below. A proximal portion of the outer sheath 115 is shown extending into the distal end 116 of the handle 100 through an opening 121 located at the distal end 116 of the handle 100 and entering into the passageway 120 of the handle 100. The compact geometry of the handle 100 enables the user to use a single hand when deploying the self-expandable prosthesis. Additionally, the handle 100 may be symmetrically shaped, as shown in FIG. 1, such that left-handed and right-handed users can operate the handle 100.

Figure 2:
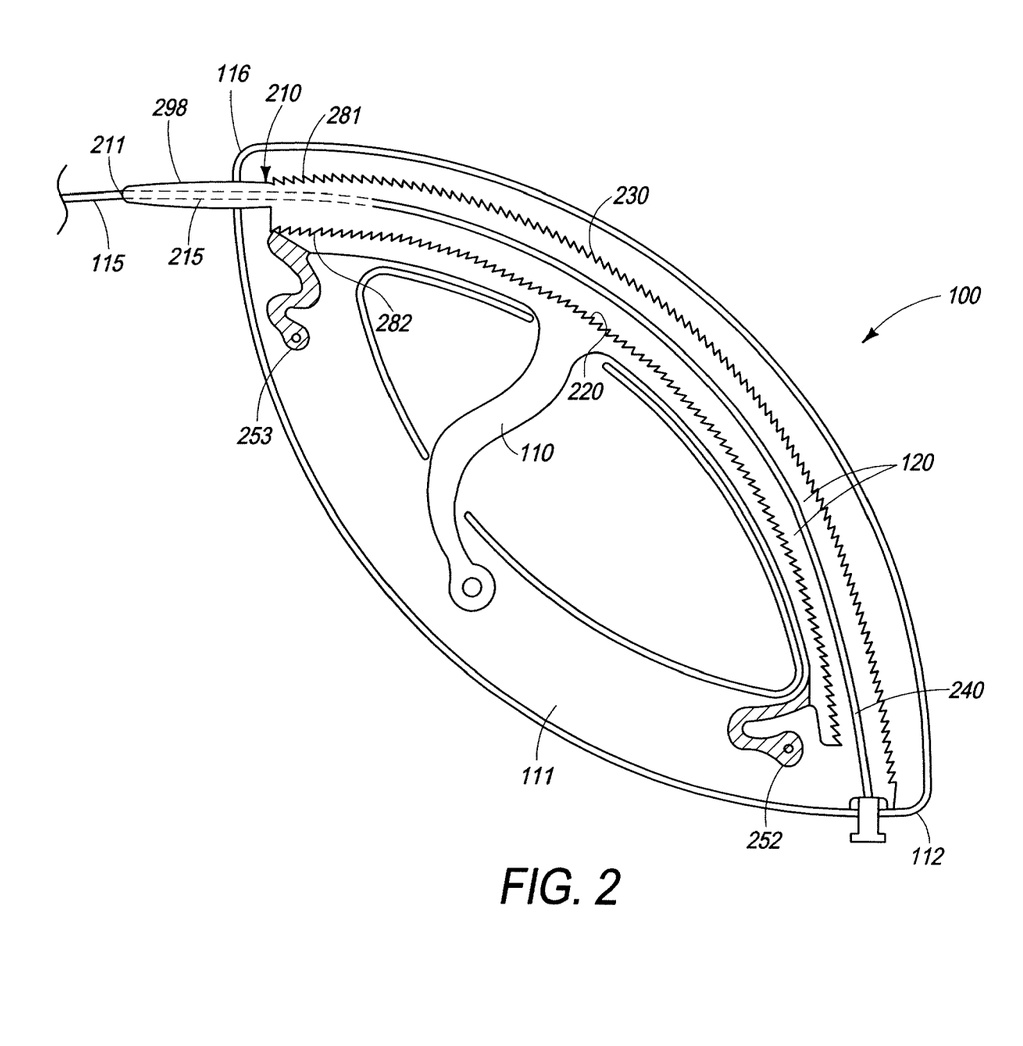
FIG. 2 shows a partial cross-sectional view of the delivery device of FIG. 1.

The inner workings of the handle 100 will now be discussed. FIG. 2 is a partial cross-sectional view of the handle 100. As can be seen, the handle 100 comprises a movable member 210, trigger rack 220, and stationary rack 230. Generally speaking, activation of the trigger 110 causes the movable member 210 to proximally retract an incremental amount, thereby pulling the outer sheath 115 an incremental amount. The distal end 211 of the movable member 210 may be assembled to a proximal end of the outer sheath 115, as shown in FIG. 2. The proximal end 212 of the movable member 210 may contain a hemostatic seal that allows movement over, and sealing against, an inner metallic cannula 240.

Still referring to FIG. 2, the inner metallic cannula 240 may be located in the open space 120 between the stationary rack 230 and the trigger rack 220. The cannula 240 may extend from the proximal end 212 of the movable member 210 to the proximal end 112 of the handle 100, and through distal opening of the handle 100 as shown in FIG. 2. An inner sheath may extend through the cannula 240. Because the proximal portion of the inner sheath may extend past the outer sheath 115, the inner cannula 240 may be needed over the inner sheath for the purpose of providing sufficient column strength such that the proximal portion of the inner sheath does not buckle due to the compressive forces it may incur during a trigger 110 stroke (i.e., the inner sheath may be in compression as the outer sheath 115 slides over the inner sheath). The proximal portion of the inner sheath is defined as that portion of the inner sheath disposed within the handle 100 and extending past the proximal end of the outer sheath 115 (i.e., the portion that is located proximal of the proximal end 212 of the movable member 210). Accordingly, the inner cannula 240 may be made from a material stronger than plastic (e.g., stainless steel) to resist buckling due to the compressive forces incurred during a trigger 110 stroke.

In the example shown in FIG. 2, the inner sheath extends to the proximal end 112 of the handle 100. An inner metallic cannula 240 may be coaxially disposed over the proximal portion of the inner sheath. The cannula 240 extends from the proximal end 212 of the movable member 210 to the proximal end 112 of the handle 100 to protect the inner sheath from compressive forces.

Alternatively, the proximal portion of the inner sheath may not be disposed within the cannula 240 and extend to the proximal end 112 of the handle 100. Rather, the proximal end of the inner sheath may be mounted to the cannula 240 at some point within the passageway 120 of the handle 100. For example, the inner sheath may be mounted to the cannula 240 at the movable member such that only the cannula 240 extends from the proximal end 212 of the movable member 210 to the proximal end 112 of the handle 100. The inner sheath and the cannula 240 preferably have the same outer diameter such that the movable member 210 smoothly moves across the interface of the inner sheath and the inner cannula 240.

FIG. 2 shows that the handle 100 comprises a stationary toothed rack 230 and a trigger movable toothed rack 220. As shown in FIG. 2, the stationary rack 230 has a downward sloping curvature (i.e., radius/arcuate curvature). The stationary rack 230 extends along the outer curvature of the handle 100 from the distal end 116 to the proximal end 112 of the handle 100. The stationary rack 230 comprises a plurality of ratcheting or directionally biased teeth that engage with a corresponding first set of teeth 281 of the movable member 210. During the pull-back of the trigger 110, the first set of teeth 281 of the movable member 210 may slip over the corresponding teeth of the stationary rack 230.

The trigger rack 220 extends along the inner curvature of the handle 100 from the distal end 116 to the proximal end 112 of the handle 100. The trigger rack 220 also has a downward sloping curvature (i.e., radius/arcuate curvature). It comprises a plurality of ratcheting or directionally biased teeth that engage with a corresponding second set of teeth 282 of the movable member 210. The trigger rack 220 may be movable back and forth along a curved path within the passageway 120 of the handle 100. FIG. 2 represents the starting position of the trigger rack 220 in which the outer sheath 115 is completely covering the prosthesis. During pull-back of the trigger 110, the configuration of the second set of teeth 282 between the movable member 210 and the trigger rack 220 remain unchanged (i.e., the set of teeth 282 remain engaged to the same teeth of the trigger rack 220 without slippage). Because the trigger 110 and the trigger rack 220 are preferably shown as a single component, the trigger 110 acts directly on the trigger rack 220 such that trigger rack 220 will move in the same direction that the trigger 110 moves. FIG. 2 shows that the trigger rack 220 is biased in its distal, starting position. Referring to FIG. 2, activation of the spring-loaded trigger 110 causes the trigger rack 220 to be pulled back in an arc-like path (see arrows on the movable member 220 of FIGS. 5 and 7). The pull back of the trigger rack 220 also pulls back the movable member 210, and the second set of teeth 282 of the movable member 210 remain engaged to the corresponding teeth of the trigger rack 220. The first set of teeth 281 of the movable member 210 slip past the corresponding teeth of the stationary rack 230 when the trigger 110 is pulled back.

When the user's finger is removed from the trigger 110, the trigger 110 and the trigger rack 220 move in the distal direction (i.e., in the position shown in FIG. 2) and return to their biased, starting position. During the return of the trigger rack 220 to its biased starting position, the teeth of the trigger rack 220 slip past the second set of teeth 282 of the movable member 210. However, the movable member 210 will not return to its distal starting point shown in FIG. 2. Rather, it will be held captive in its new position by the teeth of the stationary rack 230 such that incremental movement of the movable member 210 has been achieved as shown in FIGS. 6 and 7. The amount of incremental movement of the movable member 210 may be directly equivalent to the distance the trigger 110 has been pulled back. Varying the stroke of the trigger 110 may vary the retraction of the movable member 210 and hence the amount that the outer sheath 115 is pulled back. For example, the trigger 110 may be pulled completely rearward such that the movable member 210 moves proximally the maximum number of ratchet clicks per trigger stroke before the trigger 110 is released to return to its biased position for the next trigger stroke. Alternatively, the trigger 110 may be pulled rearward only a small amount such that the movable member 210 moves proximally only a small number of ratchet clicks per trigger stroke (e.g., about 1 or about 2 ratchet clicks) before the trigger 110 is released to return to its biased position prior to the next stroke.

In order to allow the compliance necessary for the disengagement and engagement of the first set of teeth 281 and second set of teeth 282 of the moveable member 210 with the corresponding teeth of the trigger rack 220 and stationary rack 230, springs may be used. FIG. 2 shows proximal return spring 252 located at the proximal end 112 of the handle 100 and distal return spring 253 located at the distal end 116 of the handle 100. The springs 252, 253 are attached to the housing 111 of the handle 100. The springs 252, 253 are configured to distally return the trigger rack 220 to its biased, starting position after release (i.e., deactivation) of the trigger 110 and allow the compliance necessary for the teeth 281, 282 to engage and disengage.

Figure 3:
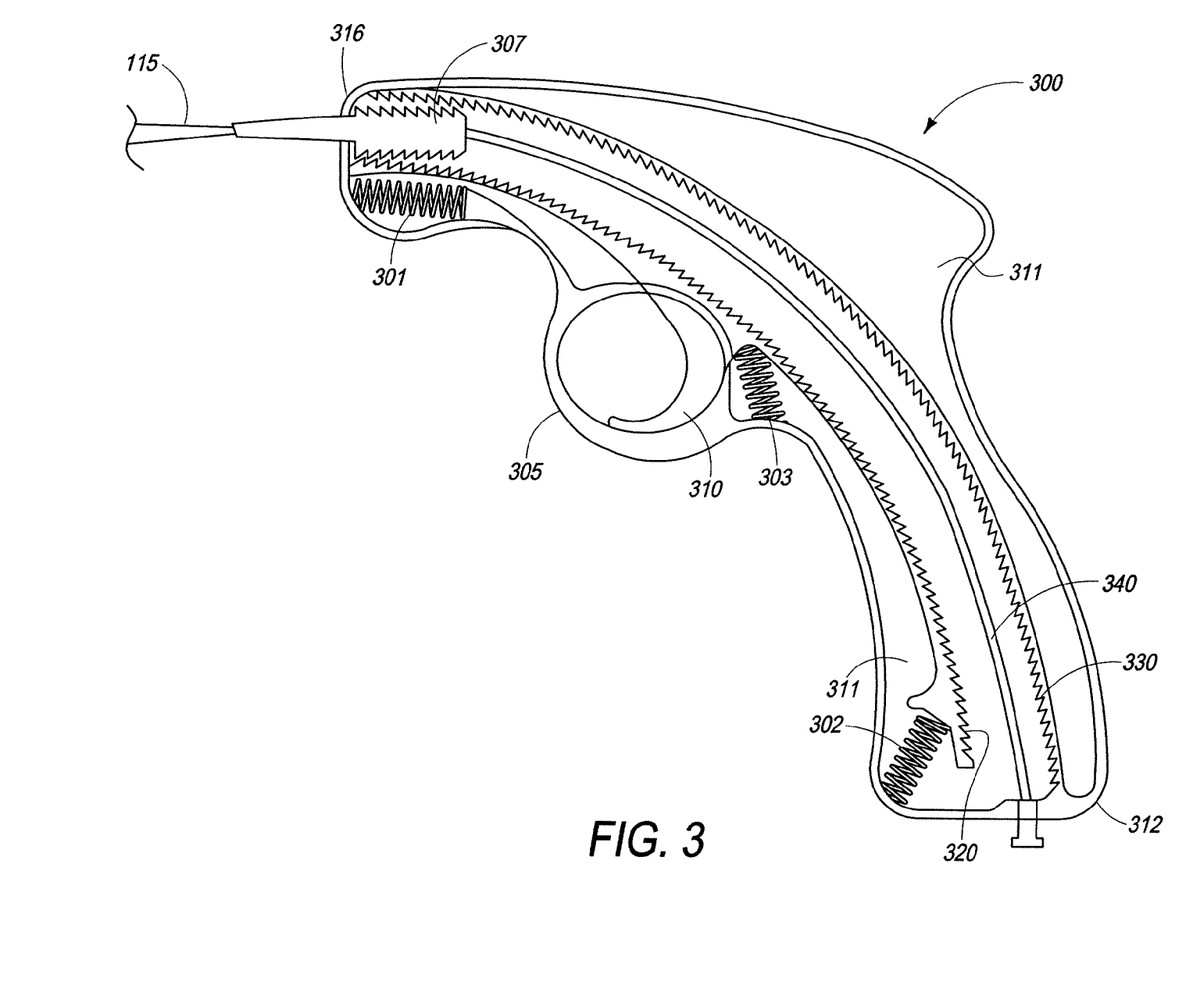
FIG. 3 is a partial cross-sectional view of another type of delivery device.

Alternatively, coil may be used to move the trigger rack 320, as shown in the embodiment of FIG. 3. FIG. 3 shows a control handle 300 in which the trigger 310 is spring-loaded with a trigger coil 303, in which the trigger coil 303 is disposed behind the trigger 310. A proximal coil 302 and a distal coil 301 are located at the proximal and distal ends 312, 316 of the handle 300 to move the trigger rack 320 back and forth. The coils 301, 302, 303 are positioned between the housing 311 of the handle 300 and the trigger rack 300. The trigger 310 may be contained in a trigger housing 305 through which a user may put his or her finger to activate the trigger 310. Preferably, the coils 301, 302, 303 are compression springs in which they are partially expanded under compression. Unlike the design of the handle 100 of FIG. 2, the handle 300 of FIG. 3 may be designed as a pistol.

Figure 9:
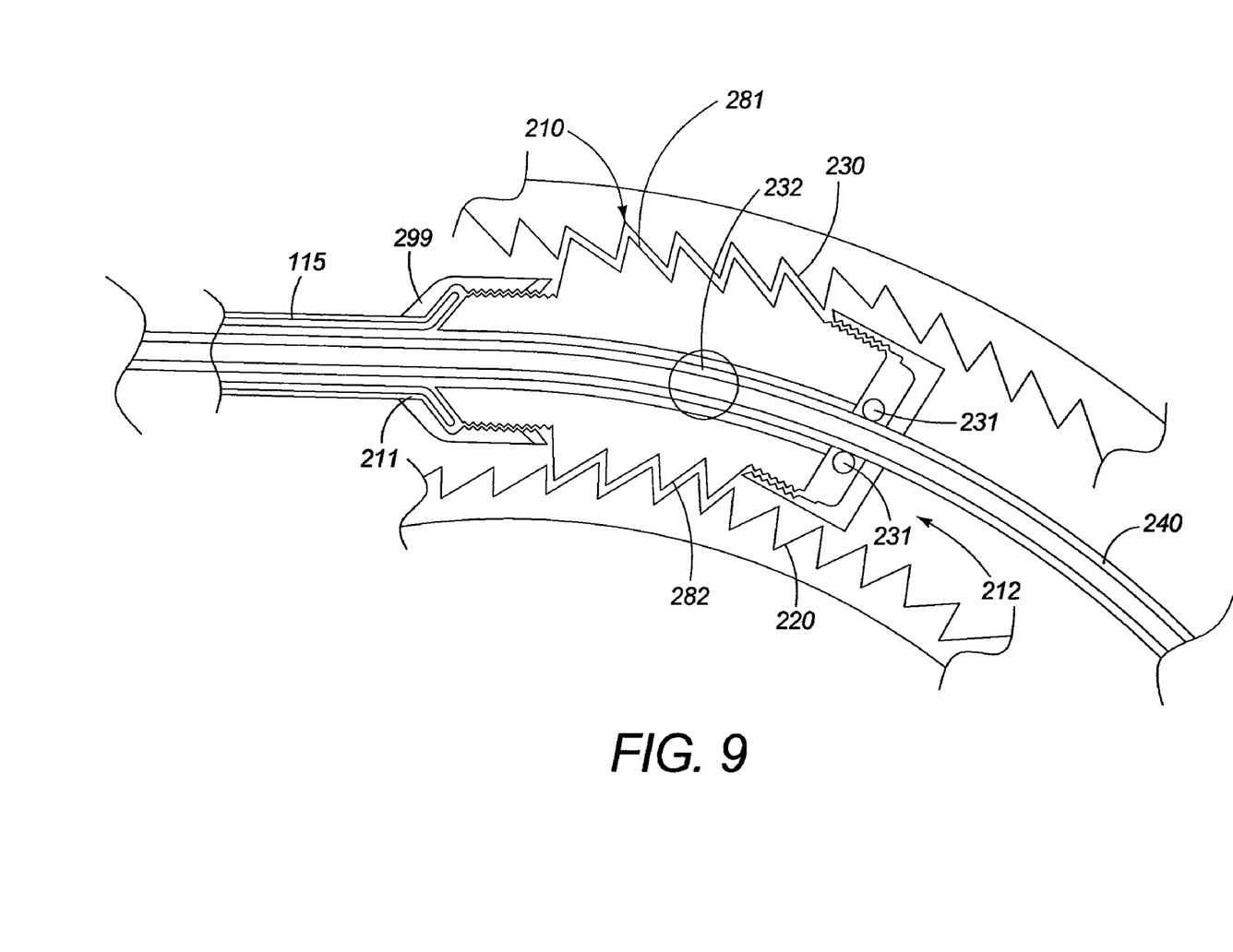
FIG. 9 is a side view of a movable member of a delivery device.

The movable member 210 as shown in FIG. 2 is disposed within the passageway 120 of the handle 100. As mentioned, the movable member 210 has a first set of teeth 281 that is ratchedly engaged to the stationary rack 230 and a second set of teeth 282 that is ratchedly engaged to the trigger rack 220 (FIG. 2 and FIG. 9). A distal end 211 of the movable member 210 is assembled to the proximal end of the outer sheath 115, as shown in FIG. 2 and FIG. 9. FIG. 9 shows that the outer sheath 115 may be flared and retained by a flare-nut onto the tapered section 299 of the movable member 210. Other means for affixing the outer sheath 115 to the movable member 210 are contemplated and would be apparent to one of ordinary skill in the art. Retraction of the movable member 210 into the passageway 120 of the handle 100 causes corresponding incremental, controlled retraction of the outer sheath 115. The movable member 210 has a central passageway 215 that facilitates slidable movement over the underlying inner metallic cannula 240/inner sheath (FIG. 9). The central passageway 215 (FIGS. 2 and 9) also allows fluids (e.g., saline and contrast media) to flow therein during flushing, etc., but maintains hemostasis where the inner metallic cannula 240 emerges from therein.

The strain relief section 298 provides a strong junction from the outer sheath 115 to the movable member 210. As shown in FIG. 2 and FIG. 9, the strain relief 298 may be tapered and provide a transition between the movable member 210 and the outer sheath 115. The strain relief section 298 may alleviate the tension created when the movable member 210 pulls on the outer sheath 115 during a trigger stroke (i.e., activation of the trigger 110).

The proximal end 212 of the movable member 210 comprises a hemostatic element 231 which is assembled to the movable member 210 (FIG. 9). In the example of FIG. 9, the hemostatic element may contain o-rings 231 that provide a seal sufficient to prevent backflow of blood and other fluids (e.g., contrast media, saline) past this location at which the hemostatic element 231 is situated. The hemostatic element 231, as shown in FIG. 9, may provide a seal that is sufficiently fluid tight but yet compliant enough to allow the slidable movement of the movable member 210 over the inner sheath and inner cannula 240. FIG. 9 shows a side port 232 through which fluids may be injected. A hub 119 (FIG. 1) may be assembled to the side port 232 that may be grasped to manually pull the movable member 210 back into handle 100 for manual retraction of the outer sheath 115, as will be explained below. The movable member 210 may comprise multiple pieces assembled to each other or may comprise a single injection molded part.

Figure 8:
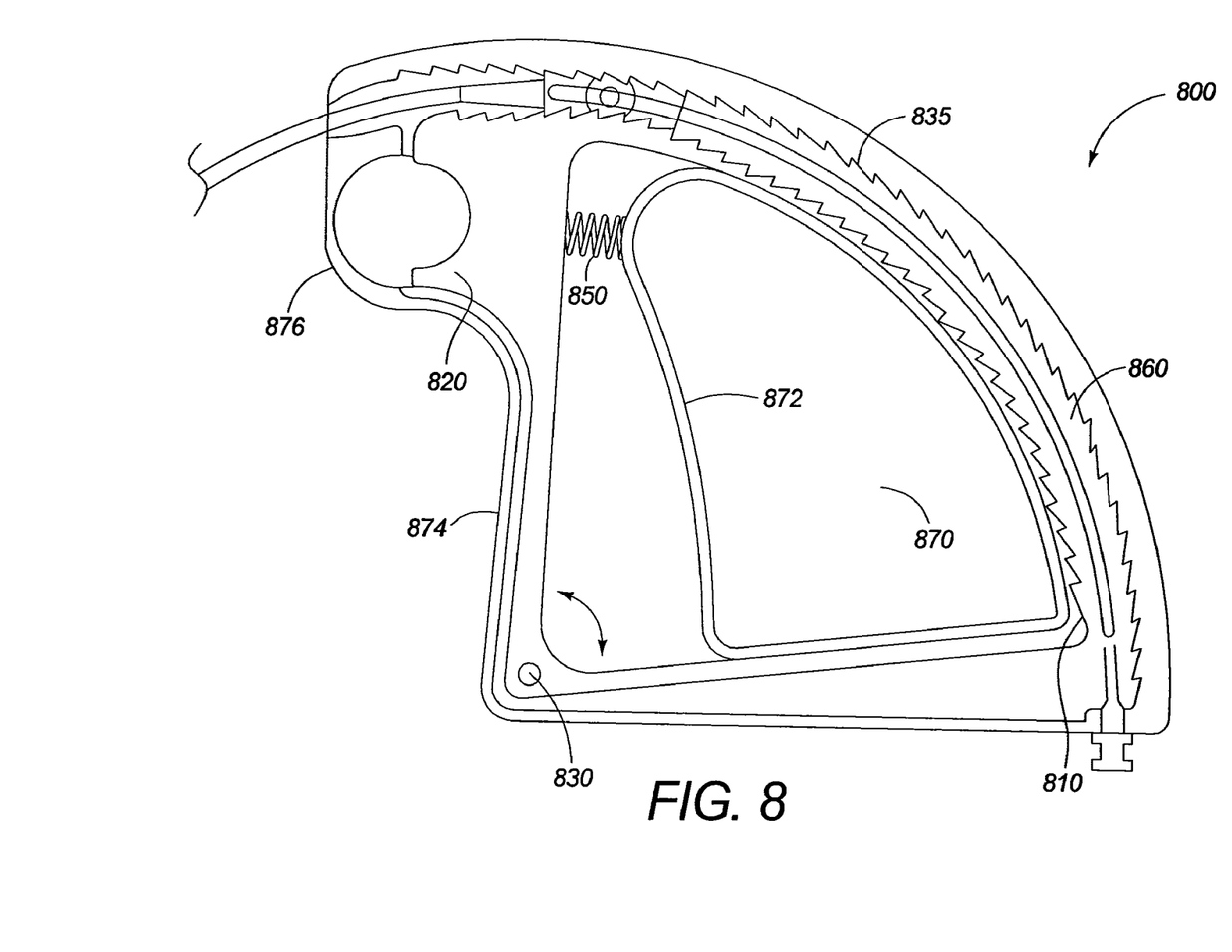
FIG. 8 shows an alternative embodiment of a control handle in which the entire trigger rack is pivotable.

FIG. 8 shows an alternative embodiment of a control handle 800. FIG. 8 shows a triangular shaped trigger rack 810 which pivots about a pin 830 located at the lower left hand corner of the control handle 800. The entire trigger rack 810 may oscillate back and forth about the pin 830 as indicated by the dual arrow. Activation of the trigger 820 causes the spring 850 that is located behind the trigger 820 to compress. Compression of the spring 850 allows the entire trigger rack 810 to pivot about pin 830 and move in a proximal direction. FIG. 8 shows the trigger 820 having been actuated a sufficient number of times such that the movable member 810 has slipped past multiple teeth of the stationary rack 835 and moved proximally within the passageway 860 of the handle 800 where it remains engaged with corresponding teeth of the stationary rack 835. FIG. 8 further shows an opening 870 through the control handle 800 below the trigger rack 810. One side of the opening 870 defines a first edge surface 872 that is located proximal from the trigger 820. A second edge surface 874 is located distal from the first edge surface 872 and below the trigger 820. The pin 830 is located between the first edge surface 872 and the second edge surface 874 and at the bottom portion of the housing 800. The trigger 820 may be contained in a trigger housing 876.

Figures 4A, 4B, 7A, 7B:
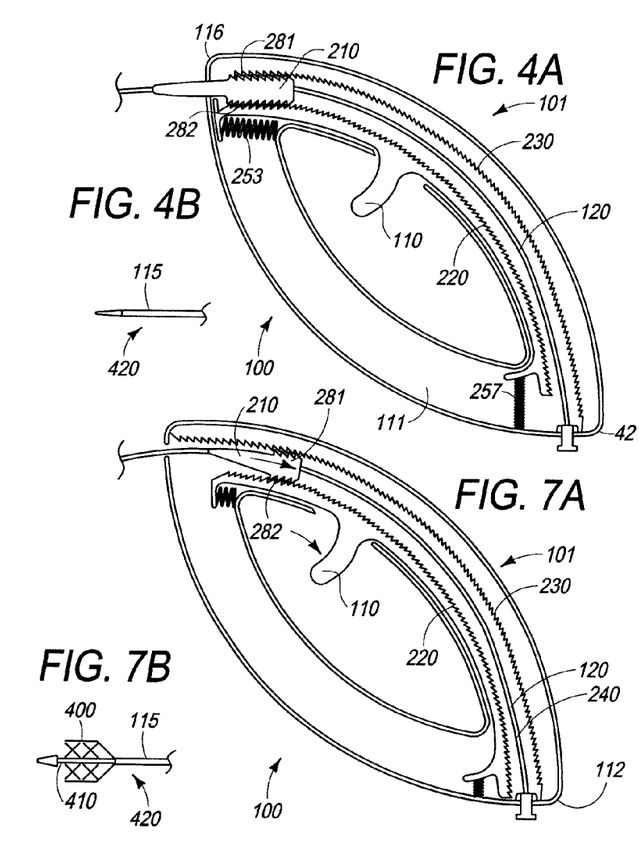

Having described the structural features of the control handle, a method of use of the control handle 100 may now be described with respect to FIGS. 4-7. A self-expanding stent 400 may be loaded between the inner sheath 410 and the outer sheath 115 along the distal end of the delivery system 101. A guide wire may be loaded through the distal opening of the inner catheter and threaded through the lumen of the inner sheath 410 to emerge from the proximal end 112 of the handle 100.

Having loaded the self-expanding stent 400 and guide wire through the delivery system 101, the delivery and deployment process may begin. The delivery system 101 comprises a stent delivery section 420 and the handle 100. The delivery section 420 travels through the body lumen during the procedure and delivers the stent 400 to a desired deployment site. The handle 100 stays outside of the body during the procedure. The handle 100 can be manipulated by the physician with a single hand to position and release the stent 400 into the body lumen. After having delivered the delivery section 420 to the target site, the deployment of the stent 400 may begin.

FIG. 4 shows the starting, biased position of the trigger rack 220 in which the trigger rack 220 is situated at the distal end 116 of the handle 100. The movable member 210 is shown ratchedly engaged to the trigger rack 220 and the stationary rack 230. The trigger 110 is positioned in its biased, starting position. At this stage, the outer sheath 115 is shown completely disposed over the inner sheath 410 and self-expanding stent 400.

Figures 5A, 5B, 6A, 6B:
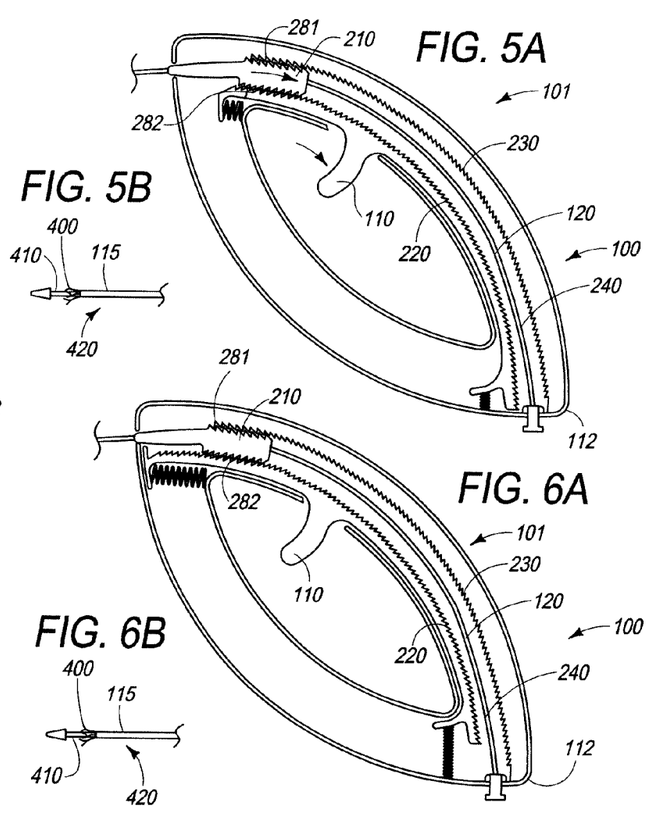

FIG. 5 shows that the trigger 110 may be activated by pulling on the trigger 110, as indicated by the arrow pointing in the proximal direction. The amount that the trigger 110 is pulled back can be varied. Varying the stroke of the trigger 110 may vary the retraction of the movable member 210 and hence the amount that the outer sheath 115 is pulled back. In the example of FIG. 5, the trigger 110 is only partially pulled back. The trigger 110 acts directly on the trigger rack 220 such that the trigger rack 220 may move in the same direction that the trigger 110 moves. Pulling on the trigger 110 may cause the trigger rack 220 to be pulled an amount equivalent to the amount that the trigger 110 may be pulled back. The retraction of the trigger rack 220 may also pull the movable member 210, as indicated by the arrow along the moving member 210 pointing in the proximal direction. The movable member 210 travels in an arc-like path. The second set of teeth 282 of the movable member 210 remain engaged to the corresponding teeth of the trigger rack 220. The first set of teeth 281 of the movable member 210 slip past the corresponding teeth of the stationary rack. Return springs 252 and 253, which are located at each of the ends of the trigger rack 220, help to bias the trigger rack 220 forward or distally and tightly engaged relative to the movable member 210. Because the movable member 210 is assembled to the outer sheath 115, retraction of the movable member 210 causes the movable member 210 to pull on the outer sheath 115 such that the outer sheath 115 proximally retracts an incremental amount. FIG. 5B shows that the outer sheath 115 has been proximally retracted, such that a portion of the self-expanding stent 400 has been exposed. A ring may be located on the inner sheath 410 to prevent the stent 400 from sliding back with the outer catheter 115.

FIG. 6 shows that the trigger 110 is deactivated such that the trigger 110 moves distally, as indicated by the distal arrow, and returns to its biased starting position. As the trigger 110 is connected to the trigger rack 220, the trigger rack 220 also returns to its starting position. The teeth of the trigger rack 220 slip past the second set of teeth 282 of the movable member 210. Return coils 256 and 257 distally return the trigger rack 220 to its starting, biased position (FIG. 4). The movable member 210 does not return with the trigger 110 because the first set of the teeth 281 of the moveable member 210 remains ratchedly engaged with the teeth of the stationary rack 230 to constrain the movable member 210 in the position shown in FIG. 6.

FIG. 7 shows that the trigger 110 may be activated a second time to further proximally move movable member 210 and trigger rack 220 in an arc-like path within the passageway 120 of the handle 100. The moveable member 210 ratchedly engages and slips past teeth of the stationary rack 230 to arrive at the position shown in FIG. 7. As the movable member 210 proximally moves within the passageway 120 of the handle 100, it pulls on the outer sheath 115 to further proximally retract the outer sheath 115 and expose a larger portion of the self-expanding stent 400, as shown in FIG. 7. Deactivation of the trigger 110 causes the trigger 110 and trigger rack 230 to return to their starting, biased position of FIG. 4 so that another trigger stroke may be actuated. Movable member 210 remains in the position shown in FIG. 7.

Repeated actuation of the trigger 110 may occur until the moveable member 210 proximally moves sufficiently along the passageway 120 of the handle 100 to completely retract the outer sheath 115 from the stent 400 such that the entire self-expanding stent 400 may be exposed. At this point, the stent 400 may not be constrained by the outer sheath 115 and thus may radially expand within the body lumen.

As an alternative to actuating the trigger 110 to retract the outer sheath 115, a knob 119 (FIG. 1) located on the movable member 210 may be manually pushed back in a single smooth and sweeping motion to deploy the stent 400 relatively quickly as compared to the incremental deployment via trigger actuation. Referring to FIG. 1, a knob 119 is shown assembled to the movable member 210. The user may grab the knob 119 and pull it back towards the proximal end 116 of the handle 100. A combination of incremental control using the trigger 110 and coarse control using the knob 119 may be utilized during the procedure. For example, initial retraction of the outer sheath 115 may be achieved via the trigger 110 to achieve incremental movement of the outer sheath 115. Incremental and gradual deployment during the initial part of the procedure may help the user deploy the distal-most portion of the stent 400 such that it can no longer change longitudinal position. After determining that the stent 400 is anchored in the correct location, the stent 400 may be rapidly deployed via pulling back the knob 119 in a single sweeping motion.

The above described embodiments are advantageous over existing delivery devices from the standpoint that less sliding friction is generated utilizing the control handles described for retraction of the outer sheath 115.

Other means of ratcheted engagement of the movable member 210 with the trigger and stationary racks 220 and 230 are contemplated without deviating from the scope of the invention. For example, the movable member 210 may comprise a flat spring which replaces the first and second set of ratchet teeth 281, 282 shown in FIG. 9. The flat spring may extend about moveable member 210 and have flared ends on opposite ends of the movable member 210 which ratchetedly engage with trigger and stationary racks 220 and 230.

It is therefore intended that the above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A delivery device, comprising:
   a handle comprising a trigger and a housing;
   a trigger rack affixed to the trigger, the trigger rack being movable back and forth within the handle and being pivotable about a pivot point, the trigger rack thereby being rotatable along a curved path around the pivot point;
   a stationary rack affixed to the housing, wherein the trigger rack and the stationary rack comprise a downward sloping curvature;
   a passageway between the trigger rack and the stationary rack having a downward sloping curvature; and
   a movable member disposed within the passageway, the movable member being ratchedly engaged to the trigger rack and the stationary rack along the entire downward sloping curvature of the passageway, a distal end of the movable member adapted to be assembled to a proximal end of an elongate sheath, wherein the ratcheted engagement of the movable member with the trigger rack and the stationary rack is configured to proximally retract the elongate sheath as the trigger is actuated.

2. The delivery device of claim 1, further comprising an inner sheath adapted to be disposed within the elongate sheath, the inner sheath extending into the passageway of the handle and remaining stationary.

3. The delivery device of claim 2, further comprising an inner metallic cannula, a proximal end of the cannula being affixed to the handle and a distal end of the cannula being affixed to the inner sheath.

4. The delivery device of claim 1, wherein the trigger and the trigger rack are spring biased.

5. The delivery device of claim 1, the pivot point being located at a bottom portion of the housing.

6. The delivery device of claim 1, wherein the handle comprises a trigger housing.

7. The delivery device of claim 1, wherein the movable member comprises a hemostatic element.

8. The delivery device of claim 1, wherein a proximal end of the elongate sheath is connected to a distal end of a strain relief section.

9. The delivery device of claim 1, in combination with a self expandable stent in a generally compressed configuration adapted to be disposed between the elongate sheath and an inner sheath.

10. The delivery device of claim 1, the moveable member connected to a knob, wherein the knob is adapted to be manually pushed back towards a proximal end of the handle.

11. The delivery device of claim 1, further comprising an opening through the handle disposed below the trigger rack, one side of the opening defining a first edge surface disposed proximally from the trigger, a second edge surface disposed distally from the first edge surface and below the trigger, and the pivot point being disposed between the first edge surface and the second edge surface.

12. The delivery device of claim 11, further comprising an inner sheath adapted to be disposed within the elongate sheath, the inner sheath extending into the passageway of the handle and remaining stationary, wherein the trigger and the trigger rack are spring biased, the pivot point being located at a bottom portion of the housing, and the handle comprises a trigger housing.

13. A delivery system, comprising:
   a handle comprising a trigger and a housing;
   an inner sheath extending to the handle,
   an outer sheath coaxially disposed over the inner sheath and extending into the handle;
   a prosthesis disposed between the inner sheath and the outer sheath;
   a trigger rack affixed to the trigger, the trigger rack being movable back and forth along a path within the handle and being pivotable about a pivot point, the trigger rack thereby being rotatable along a curved path around the pivot point;
   a stationary rack affixed to the housing, wherein the trigger rack and the stationary rack comprise a downward sloping curvature; and
   a passageway between the trigger rack and the stationary rack having a downward sloping curvature; and
   a movable member disposed within the passageway; the movable member being ratchedly engaged to the trigger rack and the stationary rack along the entire downward sloping curvature of the passageway, a distal end of the movable member affixed to a proximal end of the outer sheath, wherein the ratcheted engagement of the movable member with the trigger rack and the stationary rack proximally retract the outer sheath and deploy the prosthesis.

14. The delivery system of claim 13, wherein a proximal end of the inner sheath is affixed to an inner metallic cannula.

15. The delivery system of claim 13, wherein the inner catheter comprises a proximal portion and a distal portion, the proximal portion disposed in the passageway, the proximal portion extending within an inner metallic cannula.

16. The delivery system of claim 13, wherein the movable member is slidably disposed over an inner metallic cannula.

17. The delivery system of claim 13, wherein a hemostatic element is affixed to a proximal end of the movable member.

18. The delivery device of claim 13, further comprising an opening through the handle disposed below the trigger rack, one side of the opening defining a first edge surface disposed proximally from the trigger, a second edge surface disposed distally from the first edge surface and below the trigger, and the pivot point being disposed between the first edge surface and the second edge surface.

19. The delivery device of claim 18, wherein the inner sheath extends into the passageway of the handle and remains stationary, the trigger and the trigger rack are spring biased, the pivot point being located at a bottom portion of the housing, and the handle comprises a trigger housing.

* * * * *